United States Patent [19]

Lee et al.

[11] Patent Number: 5,183,805
[45] Date of Patent: Feb. 2, 1993

[54] BIOACTIVE EGF PEPTIDES FOR PROMOTION OF TISSUE REGENERATION AND CANCER THERAPY

[75] Inventors: Jin S. Lee; Mark Blick, both of Houston, Tex.

[73] Assignee: Board of Regents, The University of Texas System, Austin, Tex.

[21] Appl. No.: 567,407

[22] Filed: Aug. 13, 1990

[51] Int. Cl.$^5$ .................. A61K 37/00; A61K 37/02; C07K 5/00; C07K 7/00

[52] U.S. Cl. ........................ 514/13; 514/12; 530/325; 530/326

[58] Field of Search .............. 514/13, 12; 530/325, 530/326

[56] References Cited

U.S. PATENT DOCUMENTS 4,686,283 8/1987 Nestor, Jr. et al. ............. 530/327

OTHER PUBLICATIONS

International Search Report (1992).
Mably et al. (1985). Chemical Abstracts. 102(3), Abstract 17757z.
Mortsch et al. (1984). Chemical Abstracts. 101(3), Abstract 17554k.
WO, A1 8901489-Commonwealth Scientific and Industrial Research Organization (1989).
WO, A1 8501284-Komoriya, Akira (1985).
Cooke, R. M. et al. (1987). Nature. 327:339-341.
Komoriya et al. (1984). Proc. Natl. Acad. Sci. USA. 81:1351-1355.
Heath et al. (1986). Proc. Natl. Acad. Sci. USA. 83:6367-6371.
Gregory et al. (1975), Nature. 257:325-327.
Cohen et al. (1975). Proc. Natl. Acad. Sci. USA. 73:1317-1321.
Simpson et al. (1985), Eur. J. Biochem., 153:629-637.
Engler et al. (1988). J. Biol. Chem., 253(25):12384-12390.
Tam et al. (1986). Proc. Natl. Acad. Sci. USA, 83(21):8082-8086.
Hudgins et al. (1988), Cancer Res. 48(6):1428-1434.
Hannauske et al. (1986), Cancer Res., 48(11):5567-5570.
Nestor et al., (1985), Biochem. Biophys. Res. Commun., 129:226-232.
Bell et al., (1986), Nucleic Acids Research, 14(21):8427-8446.

Primary Examiner—Lester L. Lee
Assistant Examiner—A. M. Davenport
Attorney, Agent, or Firm—Arnold, White & Durkee

[57] ABSTRACT

A biologically active cyclic synthetic peptide analog having an amino acid sequence similar to that of native epidermal growth factor between amino acids 32-48 is revealed. The peptide has been found to mimic certain biological activities of intact native epidermal growth factor (EGF). The EGF peptide analogs of the present invention include at least one sulfhydryl bond between two cysteines of the peptide containing block termini. The peptides comprise the end of the B-loop and the C-loop characteristic of the native form of the epidermal growth factor peptide. The biological activity of the peptide provides for methods of using the peptide as an agent in wound healing and also in cancer therapy. More particularly, the described peptides are used in cancer therapeutic applications and in the promotion of wound healing, especially burn wounds and peptic ulcer disease. Methods of preparing and using the described bioactive EGF analog peptides are also disclosed. Both the D- and L- forms of the peptides' amino acids are within the scope of the described biologically active peptides.

16 Claims, 5 Drawing Sheets

Fig. 1

IMMUNE COMPLEX KINASE OF EGF-R
AFTER ADDITION OF VARIOUS BIOLOGIC RESPONSE MODIFIERS
TO A431 CELLS

BRM/CONTROL (1) 0.7 3.9 0.9 0.9 0.6 3.6

BIOACTIVE EGF PEPTIDES FOR PROMOTION OF TISSUE REGENERATION AND CANCER THERAPY

The government may own certain rights in the present invention pursuant to N. H. Grant R 23C A 39803.

BACKGROUND OF THE INVENTION

1. Field of the Invention

The present invention relates to the field of biologically active peptides, particularly the peptide known as epidermal growth factor. More specifically, the present invention relates to a surprisingly potent cyclic peptide similar in sequence to a fragment of epidermal growth factor between amino acid residues 32 and 48. This particular fragment includes the end of the B loop and the entire C loop characteristic of the native form of the EGF peptide. The present invention also relates to the field of peptide synthesis, as a method for synthesizing the EGF analog is described.

Additionally, the present invention relates to methods of using the described synthetic peptides to promote wound healing, to treat peptic ulcer disease and to inhibit growth of tumors. The present invention also relates to methods of treating particular tumors which overproduce epidermal growth factor receptor (EGF-r), so as to inhibit tumor growth. The described novel peptides are capable of serving antagonistic and agonistic roles in biological systems, and therefore are used to promote a variety of biological effects. This invention also relates to methods of using the described peptides to promote wound healing, especially in the treatment of burn wounds and peptic ulcer disease. In that the novel peptides inhibit the growth of tumors, the present invention also relates to methods of cancer therapy.

2. Description of the Related Art

Epidermal growth factor is a single-chain polypeptide having a molecular weight of 6 Kd (53 amino acid residues) and having three internal disulfide bonds. These three well characterized internal disulfide bonds of the epidermal growth factor peptide define three "loops", the A, B and C loops. Generally, the A loop is characterized between amino acid residues 1–19, while the B loop is characterized between residues 20–31 and the C loop being characterized as between residues 34–43[2].

The disulfide bonds have been found to be required for retention of complete biologic activity in EGF peptide fragment analogs. Heath and Merrifield (1986)[3] examined several synthetic peptides, and found low activity in the isolated "B" loop, (i.e. 0.001% that of EGF) and lesser activity (through above background) in the isolated A and C loops. Korimaya et al. have found that the linear and cyclic forms of the isolated B loop peptide were active in both EGF-receptor binding and biological stimulation (mitogenesis) in cell culture, but the activity was very low (0.003% of native EGF), while the other loops were described as being inactive[2]. It is already known that the residues 49–53 contribute little to the biological effects of EGF[1].

Several other studies have demonstrated that the immediate amino-terminal and carboxy-terminal amino acids are not required for activity of EGF (Gregory, (1975)[4], Cohen and Carpenter, (1975)[5], Hollenberg and Gregory, (1980)[6]; Simpson, et al. (1985)[7]. Recently, site-directed mutagenesis has identified key residues important to the biological activity of EGF, with the most critical being tyr 29 and leu 47 (Enger, et al., (1988), Gregory et al. (1988)[8].

The EGF peptide is already known to be a powerful nitogenic agent for a variety of cells in culture (Schlessinger, J. et al. (1983)[22]. Human EGF (hEGF), also known as urogastrone, has also been found to inhibit gastric acid secretion in vivo (Gregory, H., (1975)[4]. EGF is also known to be a powerful stimulator of cell proliferation (id.). In particular, EGF has been shown to stimulate the growth of epithelial cell tissue in a variety of preparations[23].

Peptide growth factors play important roles in several growth-regulatory processes. Two of the best characterized growth factors are the peptides EGF and transforming growth factor alpha (TGF-α)[18,11]. Transforming growth factor-α is a biologically active substance, the structure and function of which are closely related to EGF. Transforming growth factor-α (TGF-α) has similar binding affinity to EGF-R as does EGF (De Larco, J. E. et al.,(1978)[11]. These results have led to many studies attempting to synthesize partial peptide sequences of EGF, as well as TGF-α in an effort to define which part of the growth factor is essential for biologic activity.

EGF has also been found to be mitogenic for many types of normal and transformed cells, and may play a role in wound healing. TGF-α, although first described as present in the supernatant of retrovirus-transformed cells, is now known to be a normal mediator of angiogenesis, epidermal regrowth, and formulation of granulation tissue in vivo. Additionally, TGF-α is produced in many human tumors, where it may function to promote autocrine stimulation of tumor cell growth[17].

Peptides EGF and TGF-o both initiate their actions by binding the same receptor, termed epidermal growth factor receptor (EGF-R), which is a glycosylated, transmembrane protein of 170 kd molecular weight[19]. EGF-R has an intrinsic tyrosine kinase activity, which is rapidly stimulated by binding of either EGF or TGF-α, an essential event to signal transduction via these peptides[20].

EGF-R is related to the viral oncogeny, v-erb B, and is overexpressed in many human tumors, including brain[14], bladder[15], breast[16], and squamous cell carcinomas of the head, neck[21] and lung. Thus, EGF-R "activation" is an important regulatory event in stimulating the division of many normal cells as well as in the aberrant growth of some tumor cells. For these reasons, the interactions of EGF and TGF-α with EGF-R have received intense study in the last decade. Complete EGF peptides, and antibodies which mimic their action, have been used in such diverse processes as screening for tumoricidal activity[22] and promotion of wound healing[23]. However, use of these intact EGF peptides has been limited, due to their instability, lack of target specificity, and a lack of understanding of their tertiary structure.

Approaches to surmount these various problems have focused on synthesis of biologically active small peptides from the EGF and TGF-α sequences, which can then be modified to yield more stable molecules. Biological activity of previously reported EGF peptide fragments is very low[1-3], and therefore a need remains for the synthesis of more bioactive forms. Peptide analogs already tested in the art have been found to be of varying potencies, some having greater bioactivity than others. However, a peptide having sufficient bioactivity so as to be a therapeutically effective clinical pharmaceutical agent has yet to be synthesized.

The possibility of preparing a biologically active analog of defined regions of EGF offers the possibility of leading to the generation of new anti-cancer drugs. Additionally, such a peptide also presents a potentially useful therapeutic agent for the promotion of wound healing, especially as a specific treatment for burn patients and treatment of peptic ulcer disease. The development of effective methods for treating tumors which overexpress EGF-R, including squamous cell carcinomas of the lung, head and neck, would also be made possible with the isolation and synthesis of such a bioactive peptide as an anti-cancer therapeutic agent. The development of second generation peptides therefrom would also present a significant advancement in the options available in cancer therapy. It is contemplated the use of such a peptide would constitute an effective anti-cancer agent devoid, of the many side effects attendant currently practiced cancer treatments.

SUMMARY OF THE INVENTION

The present invention describes a novel peptide having the surprising ability to interact with epidermal growth factor receptor. The capability of EGF peptide analogs to effectively bind at least part of the EGF receptor is believed to exist in the closely defined peptide analog of the present invention. Applicants have identified a sequence of the epidermal growth factor peptide and prepared a particularly biologically active EGF cyclic peptide analog. This peptide analog includes the end portion of the B loop and the entire C loop characteristic of the native epidermal growth factor (EGF). More particularly, the peptide analogue includes those amino acids characteristic of the native EGF peptide between amino acids 32 and 48.

Applicants' experimental data presented herein demonstrates that the described cyclic peptide comprising the end of the B loop and the C loop has a 100-fold greater biological activity than any other EGF peptide analog thus far synthesized.

Additionally, the described EGF peptide analogs have been shown to inhibit ornithine decarboxylase activity with over two magnitudes the inhibiting activity of other EGF peptide analogs heretofore described or synthesized.

The peptide analogs of the present invention in a particularly preferred embodiment is comprised of an amino end and a carboxyl end. The amino end of the peptide further comprises an acetyl group. The carboxyl end of the peptide further comprises an amide group. In another preferred embodiment of the present invention, the peptide is characterized by an amino acid substitution at its 6 position with phenylalanine (F), where tyrosine (Y) typically exists (6 position aa residue 37 of the aa 32-48 segment). This particular embodiment of the invention may be in either cyclic or linear form. This substituted peptide was found to have enhanced activity over existing EGF analogs in the parameters examined. The level of activity of the phenylalanine-substituted peptide was above the activity characteristic of other known EGF peptide analogs. The natural tyrosine form of the cyclic peptide analog exhibited more than a 100-fold enhancement of biological activity as compared to other currently described EGF peptide analogs.

Both the tyrosine and phenylalanine-substituted EGF peptide analogs were prepared and tested in both cyclic and linear form. These studies revealed that the linear form of each peptide analog had minimal activity in the parameters examined.

In one embodiment, the EGF peptide analog of the present invention is a cyclic peptide in which phenylalanine is substituted for the tyrosine at position 37 between aa 32 and aa 48 segment of the native peptide. Cyclization was achieved by at least one internal bond between two cysteines of the peptide analog.

The present invention includes EGF peptide analogs comprising the D- and L-, or a mixture of the D- and L-amino acid forms of the amino acid sequence between aa 32 and aa 48 of native EGF and its aa residue 37-phenylalanine-substituted form. The D- form of the amino acids are particularly preferred, as a peptide comprised of D-amino acids is a much more stable therapeutic agent in vivo and would also be expected to have a longer shelf life. Peptides with D-amino acids are likely to have greater retention of their biological activity in vivo when injected because the D-amino acids are not recognized by naturally occurring proteases of the animal.

The present invention also includes methods of synthesizing the described novel peptides, as well as methods of using the synthetic peptides to promote wound healing and to inhibit tumor growth. The described peptides are to be used as a therapeutic agent in a method for treating tumors which overexpress EGF-r. For use as such a therapeutic agent, the peptide analog is used in conjunction with a delivery system, to which the peptide is coupled.

By way of example only and not limitation, the delivery systems of the present invention may include coupling of the peptide analog to diphtheria toxin or coupling to a monoclonal antibody.

While the relatively short length of the claimed peptide is believed to reduce the peptides' susceptibility to cellular degradation, the use of a coupling system is preferred in one embodiment of the invention to prevent or decrease even more any degradation of the peptide and thus prolong its bioactivity in vivo.

The present peptides are contemplated to be effective as an anti-cancer agent against tumors which overexpress EGF-r. Tumors against which the disclosed peptides are expected to be the most effective include squamous cell carcinomas of the lung, head and neck, where over-expression of EGF-R is greatest and frequent. Other tumors in which EGF-R is overexpressed comprise tumors of the brain[15], bladder[16], and breast[17].

An object of the present invention is to design a biological compound which is capable of binding EGF receptor. A second object of the invention is to design a biological compound which serves as an antagonist for transforming growth factor-α (TGF-α). Transforming growth factor alpha is a molecule which is aberrantly produced in many tumors, and exerts its biological effect by binding EGF-R.

Transforming growth factor α (TGF-α) is similar in structure to the EGF peptide. TGF-α is produced in many human tumors where it may function to promote autocrine stimulation of tumor growth[17]. Although first described in retrovirus-transformed cells, TGF-α is now known to be a normal mediator of angiogenesis, epidermal regrowth and formulation of granulation tissue in vivo.

As a therapeutic agent to promote wound healing, the described peptides may be used in a topical treatment form to be applied externally on any compromised skin condition. For such uses, it is contemplated that the peptide be included with a carrier in a coupled form. By way of example, compromised skin conditions include external skin injuries such as burns, rashes, abrasions, and the like. In such a use, it is contemplated that about a 5 ng amount of the synthetic peptide would constitute a wound-healing promoting amount of the peptide. Most preferably, the peptide would be applied or administered topically to the wound of the animal. Use of the described peptide as a treatment to promote wound healing is contemplated to be particularly suitable in the treatment of burn wounds.

The EGF peptide analog of the present invention may be used as a therapeutic agent in the treatment of cancer or for persons with malignant disease. The peptide analog may be administered systemically or locally via intravenous (I.V.) or intraarterial routes of administration. While the peptide may be administered in any tumor inhibiting amount, preferred doses of the peptide are in the range of about 0.1 mg to about 100 mg/m$^2$ body surface area/hr. These dose represent empirical approximation, which await refinement in animal models.

The present invention also includes a novel method by which the unique EGF peptide analog is synthesized, cyclized and purified. The selected peptide fragment amino acid sequence was first synthesized by using standard peptide synthesizing techniques well known to those of skill in the art, for example, using the solid-phase technique of Merrifield (1963) (*J. Am. Chem. Soc.*, 85:2149–54).

The synthesized peptides were converted from oligomer forms of the peptide to linear monomer form peptides. Wy way of example, this was preferably accomplished by treatment with a molar excess of dithiothreotol (DTT). Monomer linear forms of the peptide were then isolated by column chromatography, and then fractionated by column chromatography to remove polymer forms. The linear monomer forms of the synthesized peptides were then cyclized using $K_3FeCN_6$ as described by Chang et al. (1980)[12] and Rivier et al. (1974)[13]. More particularly, the peptides were cyclized by joining at least two cysteines within the peptide. This joining created a disulfide bridge bonding the internal cysteines. The resin is a source of the original peptides. It is stored at room temperature under anhydrous condition to produce additional peptide. The resin must be processed by hydrofluoric acid treatment, acid extractions, cyclization and finally purification.

The purification of the synthesized peptide included an additional fractionation of the cyclic peptide as a further purification step to remove organic substances. Most preferably, this further purification step was accomplished on a polystyrene column (XAD-1). Additional HPLC purification (fractionation) was performed as a final step of purification in order to eliminate any incomplete peptides or free amino acids. Peptides so further purified achieved a purity level of >99%.

Amino acid and HPLC analysis were performed on the cyclic peptide analog products to validate the identity of the peptide obtained by a measure of its biological activity. Specifically, the preparation of peptides was tested for the presence of that biological activity characteristic of the native EGF peptide. Synthetic peptides having an amino acid sequence characteristic of the native EGF peptide between aa32 and aa48 or a 6-position (aa residue 37) phenylalanine-substituted form of the native peptide sequence between aa32 and aa48 were tested.

The cyclization of the peptide analog is accomplished between the two cysteines in the amino acid sequence, with an S-S-bond ultimately being formed to bridge the two cysteines of the molecule. While many methods exist by which an amino acid sequence can be cyclized, the most preferred method of the present method includes the use of $K_3Fe CN_6$.

Preparation of the substituted form (aa residue 37) of the amino acid sequence of the described epidermal growth factor peptide analog includes the initial synthesis of a peptide. This peptide comprises the amino acid sequence characteristic of native EGF between aa32 and aa48, except that the tyrosine at aa residue 37 is deleted and a phenylalanine is substituted therefore in the peptide. This is accomplished using the Merrifield process for synthesis, as was described for the preparation of the unsubstituted peptide.

For purposes of this application the term "biologically active peptide" includes all peptides which are capable of binding EGF receptor. Relative biological activity of a peptide also may reflect the activity of the peptide in immune complex kinase assays, the ability to inhibit ornithine decarboxylase activity, mitogenic stimulation activity, ability to induce EGF-r phosphorylation in vivo and action in the phosphorylation of calpactin. The term "a tumor inhibiting amount" of the peptide is an amount of EGF peptide sufficient to reduce tumor growth.

The mechanism by which the described peptides function to reduce or inhibit tumor growth is believed to be via the binding of the synthetic peptide to cellular receptors for epidermal growth factor. As a result, EGF receptors, which are "activated" even in the absence of ligand or in the presence of small amount of ligand due to clustering on the cell surface (Maxwell), are internalized, resulting in growth inhibition.

While not entirely clear, the mechanism by which the described peptides function to promote wound healing is postulated to be the same mechanism by which EGF and TGF-α function normally, i.e. stimulating the genetic program for epidermal cell division.

The following abbreviations are used throughout the Specification:

| | |
|---|---|
| Ala or A = | alanine |
| aa = | amino acid |
| Arg or R = | arginine |
| Asn or N = | asparagine |
| Asp or D = | Aspartic acid |
| Cys or C = | cysteine |
| EGF = | Epidermal growth factor |
| EGF-r = | epidermal growth factor receptor |
| Gln or Q = | glutamine |
| Glu or E = | glutamic acid |
| Gly or G = | glycine |
| Ile or I = | isoleucine |
| Leu or L = | leucine |
| Lys or K = | lysine |
| Met or M = | methionine |
| Phe or F = | phenylalanine |
| Pro or P = | proline |
| Ser or S = | serine |
| TGF = | transforming growth factor |
| TGF-α = | transforming growth factor alpha |
| Trp or W = | tryptophan |
| Val or V = | valine |

-continued

| His or H = | histidine |
| Tyr or Y = | tyrosine |
| Thr or T = | threonine |

BRIEF DESCRIPTION OF THE DRAWINGS

FIG. 1 - Kinetics of EGF-R stimulation by synthetic peptides. To semi-confluent A431 cells (grown in 0.1% FCS), indicated concentrations of cyclic (peptide A) or linear (peptide D) peptide with tyr at position 6 was added at a concentration of 20 ng/ml for 10 min at 37° C. Cells were harvested, lysed, EFG-R was immunoprecipitated, immune complex kinase assays were performed, and proteins resolved as described in FIG. 1. As in FIG. 1, relative intensities are displayed at the bottom of the Figure. This figure compares preliminary kinetics of kinase stimulation after the addition of the active cyclic and less-active linear peptide to A431 cells. Immune complex kinase of EGF-r after addition of various biological response modifiers to A431 cells is shown. Peptide "A" represents the cyclic peptide containing the natural tyrosine at position 6 (i.e. #37 of native EGF). Peptide "D" represents the linear peptide analog with tyrosine at position 6 (i.e. #37 of native EGF). In very preliminary analysis of the kinetics of stimulation, the cyclic peptide (labeled peptide "A") showed maximum stimulation of kinase activity after 15 minutes.

FIG. 2—Immune complex kinase of EGF-R after addition of biologic response modifiers. A431 cells at approximately 70-80% confluency were lysed in a detergent-containing (RIPA) buffer, and clarified by centrifuging at 10.000×g for 10 min. EGF-R was immunoprecipitated by incubation of lysates with monoclonal antibody R1 for 2 hours at 4° C. Immune complexes were harvested after 15 min. incubation with 50 μl Pansorbin. For kinase assays, complexes were washed in RIPA buffer, then resuspended in 50 μl 1 0.1% Triton X-100 in 20 mM HEPES, pH 7.0, with the addition of 100 μm sodium vanadate. To the complexes, biologic response modifiers were added at the concentrations indicated in the Figure. After 10 min. incubation, kinase reaction was initiated by addition of 50 μl of 20 mM HEPES containing 10 μCi $\gamma-^{32}p$ ATP. Reaction was allowed to proceed at 25° C. for 10 min., and terminated by addition of RIPA buffer. Radioactive complexes were washed, and EGF-R was resolved by SDS-PAGE (8% polyacrylamide gels) followed by autoradiography. Peptide A—cyclic peptide with tyr at position 6 (i.e., position #37 of the native EGF sequence); Peptide B—linear peptide with tyr at position 6 (i.e., position #37 of the native EGF sequence). Intensities of the bands relative to untreated control Were determined by densitometric scanning, and are displayed at the bottom of the Figure. Several control peptides of unrelated sequence (in both linear and cyclic forms) failed to stimulate biologic activity of EGF-receptor in this assay (data not shown).

FIG. 3—Inhibition of $^{125}$I-EGF binding by synthetic peptides. 1×10$^5$ A431 cells were plated in each well of a 24 well tissue culture plate, and allowed to grow for 48 o hours. Cells were rinsed 3 times in cold serum-free DMEM containing 0.1% BSA and 50 mM HEPES, pH 7.4, then incubated in this medium for 45 min. at 4° C. Subsequently, varying concentrations of peptide (or unlabeled EFG) was added, followed by 20,000 cpm $^{125}$I-EGF. After 2 hours incubation, medium is removed and cells are washed two times in PBS, then solubilized in 1 ml IN NaOH at 24° C. for 18 hours. Radioactivity in the solution is determined in a gamma counter. Peptide A—cyclic peptide with tyr at position 6; Peptide B—linear peptide with tyr at position 6; Peptide C —cyclic peptide with phe at position 6. The cyclic peptide with tyr (peptide "A") showed substantial competition with $^{125}$I-EFG for binding EGF receptors, with 50% inhibition occurring at a concentration only 10-fold greater than that for unlabeled EGF. These results are significant because they represent a 100-fold greater competition for EGF receptor binding than any previously reported peptide. Unrelated peptides of similar length show very little ability to compete with EGF for EGF-r binding (data not shown). Peptide C (cyclic peptide substituting phenylalanine for tyrosine) and Peptide B (linear peptide containing tyrosine) showed marginal competition for $^{125}$I-EGF binding. The peptide most active in the kinase assay was also most active in inhibition of EGF binding.

FIG. 4—Effect of synthetic peptide pretreatment on EGF-stimulated ODC induction in ME-180 cells. Semiconfluent ME 180 cells were treated with 100 ng/ml peptide for 30 min., followed by 10 ng/ml EGF for 3 hours. Cells are pelleted, sonicated in a buffer containing 25 mM NaPO$_4$, 1mM DTT, 40 μM PLP, 0.1 mM EDTA, and centrifuged for 30 min. at 15,000 rpm at 4° C. Ornithine decarboxylase activity was determined on the supernatant by monitoring $^{14}$CO$_2$ released from 0.5 μCi of I ($^{14}$C) ornithine in a total ornithine concentration of 0.5 mM and a total volume of 0.2ml. P1—linear peptide and P2—cyclic peptide with phe at position 6; P3—linear peptide and P4—cyclic peptide with tyr at position 6. The cyclic peptide with native tyrosine at position 37 (labeled peptide 4 (P4) in the figure) inhibited by 50% ODC induction of EGF at 100-fold excess. Other peptides were less active. In the different assays performed, the same synthetic EGF peptide analog was the most active, strongly suggesting a specific interaction with native EGF.

In experiments in which peptide and EGF were mixed at the concentrations shown, stimulation of cell growth was observed at low concentrations. However, higher concentrations of native EGF no longer growth-inhibited A431 cells in the presence of 10 ng/ml synthetic cyclic EGF peptide analog. These results strongly suggest that the synthetic cyclic peptide analog does possess biologic activity characteristic of native EGF at low concentrations. Applicants' preliminary data demonstrates that the synthetic EGF cyclic peptide analog of the present invention interacts with EGF receptor. This synthetic analog may have important effects on the growth of other appropriate cell lines in addition to the A431 cell line tested. Interaction of the EGF peptide analog and native EGF appears to be complex, and will require further study.

DETAILED DESCRIPTION OF THE PREFERRED EMBODIMENTS

The present invention presents the discovery and synthesis of a novel and surprisingly bioactive peptides which comprise an amino acid sequence similar to an isolated region of native epidermal growth factor EGF peptide. The receptor-binding region of the native EGF peptide was previously described as that region present between amino acid residues 20-37 for antibody recognition (Komoriya et al. (1984) 81:1351-1355). Applicants demonstrate that the receptor-binding region of EGF resides at an amino acid region having a sequence similar to that between amino acid residues 32-48 of the native EGF peptide. The EGF receptor binding activity of the described peptides present the advantage of binding without activating the cell, thus making the peptide a potentially valuable anti-cancer agent against those tumors which overexpress EGF-receptor upon binding of tumor growth factor-α (TGF-α).

Peptide segments or fragments similar to particular sections of the native EGF peptide were selected and synthesized for the present studies by standard Fmoc synthesis protocols, employing equipment and procedures routine in the laboratory.[24] (Details of synthesis appear The following is a description of procedures used to prepare the peptide analogs of epidermal growth factor (EGF).

EGF Peptide Analog Synthesis

Selected fragments or segments of the EGF peptide (see Table 1) were prepared using the solid-phase technique of Merrifield (*J. Am. Chem. Soc.*, 85:2149-54 (1963)) using a modified Vega model 250 automated peptide synthesizer. Removal of the t-butyloxycarbonyl (t-BOC) amino acid blocking groups and separation of the peptide from the resin were accomplished by hydrofluoric acid treatment at about zero degrees for about one hour. The peptide-containing mixture was extracted with dimethyl ether to remove non-peptide organic compounds, and the synthesized peptides were extracted from the resin powder with acetic acid (about 25% w/v).

Four peptides were prepared which included linear and cyclic monomer forms of the following peptides:

I—Acetylated-NCVVGYIGERCQYRDLK-Amide (termed #37) *

II—Acetylated-NCVVGFIGERCQYRDLK-Amide (#38)

II represents phenylalanine substituted form of the synthetic EGF peptide analog.

The cyclic forms were made by joining the two internal cysteines within the peptide. The amino end and carboxy termini of the peptide analogs were blocked with acetyl and amide groups, respectively, to enhance resistance of the peptide to proteases.

Purification of Linear Monomeric Forms

After synthesis and extraction, each peptide was fractionated by column chromatography through a G-25 column to isolate the monomer form of the peptide. The peptide was first treated with a molar excess of dithiothreotol (DTT) to convert oligomer and cyclic forms to linear monomer forms before applying to the G-25 column.

Cyclization of Peptides

Peptides were fractionated by G-25 column chromatography to remove linear forms of the peptide. Peptides were further fractionated on a polystyrene column (XAD-I) to remove organic substances. Peptides were then cyclized by joining internal cysteines within the peptide using $K_3FeCN_6$ with the chemical reaction described by Chang et al. (*Int. J. Peptide Protein Res.*, 15:485-94 (1980)) and Rivier et al., (*J. Amer. Chem. Soc.*, 96:2986-92 (1974)). The peptide analogs were further processed to remove $Fe^{++}$. The presence of $Fe^{++}$ was evident as a greenish-blue color in the preparation.

Further HPLC fractionation as a final step of purification was performed and the synthetic EGF peptide analog was eluted as a single peak.

Amino Acid and HPLC Analyses

Applicants analyzed the substantially purified preparation of cyclic monomer forms of the peptide to establish the sequence of the peptide obtained as the biologically active peptide defined in Table 1, and also in its G-substituted form with phenylalanine. The amino acid and HPLC analytical analyses of these products were consistent with the expected peptide sequences. Purity of the peptide was between about 53%-57% for the cyclic monomer form of the peptide.

Model Cell Lines For Assay of Peptide Activity

At different concentrations, EGF may be mitogenic or growth-inhibiting to identical established cell lines. Therefore, testing of peptides was performed on cell lines with varying expression of cell-surface receptors. A431 cells were the primary model cell line because studies from many labs have focused on characterization of EGF-r from these cells. Applicants have also studied EGF-r expression and activity in fresh human tumors and/or cell lines from brain[18], breast[19], and squamous cell carcinomas of the head and neck (HNSCC)[20-23].

As additional models, Applicants propose to study the effect of the described peptides on two additional model HNSCC cell lines (established by Dr. P. Sacks of M. D. Anderson Hospital), because of Applicants' observed differences in EGF-r levels and response to EGF in these cell lines[20-23]. These cells should be suitable for determining biochemical activity of the peptides in important biological models, the most important first step in determining efficacy as pharmacologic agents.

Biochemistry

Peptides were first screened for their ability to alter tyrosine kinase activity in immune complex kinase assays from EGF-r on A431 cells, as previously described by the Applicants and others (Maxwell et al., 1988)[26]. This assay is very sensitive, and kinase activation is among the earliest events in mitogenesis.

Active peptides were used in assays to determine competition for binding of EGF to EGF-r from these cells. Promising peptides were then screened for induction of EGF-r phosphorylation in vivo, phosphorylation of calpactin, induction of ODC, and synthesis in model c-myc cell lines. For eventual development of peptides for biologic therapy of tumors. Applicants sought to determine the ability of these peptides to serve as antagonists for tumor cell lines, especially those which overexpress EGF receptors.

To summarize some of the results obtained from the foregoing studies, the biological activity of the peptides tested were found to have the biological activity characteristic of the unsubstituted cyclic EGF peptide analog. Particular peptides were found to exhibit between a 10 and 100-fold enhanced biological activity over other analogs heretofore synthesized. The linear form of the unsubstituted EGF peptide analog between aa32 and aa48 was found to have biological activity 10 fold greater than any peptide thus far available. The cyclic form of this unsubstituted peptide displayed an activity 100-fold greater than any other peptide heretofore described.

The following examples are presented to describe the preferred embodiments and utilities of the present invention and are not meant to limit the present invention unless specifically indicated otherwise in the claims appended hereto.

EXAMPLE 1

Synthesis of the EGF Peptide Analogues

Four peptide analogs, two peptide analogs comprising the sequence between aa 32 and aa 48 of native EGF and two peptide analogs comprising the same sequence of that peptide fragment (aa 32-aa48) except substituted at position 6 (aa residue 37) with phenylalanine in place of tyrosine were synthesized. The native EGF peptide of this region has the sequence shown in Table 1.

TABLE 1

Amino Acid Sequence Between Amino Acid Residues 32-48 of Native EGF

\* \*
asn—cys.—val—val.—gly.—tyr.—ile.—gly.—glu.—
\* \*
arg—cys.—gln.—tyr.—arg.—asp.—leu.—lys.—amide.

Each of these two different peptide sequences were synthesized in linear form and cyclized form (prepared by disulfide bridging of the two internal cysteines). Two peptides were made substituting phenylalanine for the tyrosine at aa residue #37 of the peptide, one in linear and one in cyclic form. Peptides were synthesized and partially purified as described in Merrifield et al. and as outlined supra. Further purification of the peptide was accomplished by HPLC.

Particularly preferred embodiments of the claimed peptide include an amide group at the carboxyl end and an acetyl group at the amino end (designated \*) of both the unsubstituted (tyr\*) and aa residue #37 substituted (phephenylalanine) form of the peptide.

EXAMPLE 2

Preparation of EGF Receptors From Epidermoid Carcinoma Cell Line A431

Receptors in the epidermoid carcinoma cell line A431 ATCC CRL 1555) represents the most completely studied model for the characterization of EGF receptor. This cell line has an amplified receptor gene, which makes this cell model particularly well suited for the study of the structure, activity, and biochemistry of EGF receptor.

EGF receptors from this cell line were immunoprecipitated with monoclonal antibody $R_1$ (Amersham Bioscience). Immune complexes were harvested with formalin fixed staphylococcus aureus Cowan Strain (Calbiochem). These complexes were then assayed for kinase activity in an immune complex kinase assay.

EXAMPLE 3

EGF Peptides Studied

The bioactivity of a variety of linear and cyclic forms of the synthesized EGF peptide analogs were examined by Applicants. These peptides included the following:
linear EGF-aa32 to aa48
cyclic EGF-aa32 to aa48
linear aa residue #37 substituted EGF-aa32 to aa48, position #37=phenylalanine
cyclic aa residue #37 substituted EGF-aa32 to aa48, position #37=phenylalanine Linear peptides found not to possess biological activity, as measured by receptor studies, included the following peptides; linear peptide aa 32-48—tyr at position #44, linear peptide (aa32-48)—phe at position 44. Several other peptides from other oncogeny products also failed to demonstrate biological activity in the parameters examined.

To determine a potential biological activity of the peptides, immune complex kinase assays were performed after adding various concentrations of the synthetic peptide analogs or EGF to the complexes and measuring autophosphorylation (Maxwell et al., 1988).

EXAMPLE 4

Activity of Peptides in Immune Complex Kinase Assays

The structure, activity, and biochemistry of EGF receptor has been most completely studied from the receptor in the epidermoid carcinoma cell line A431, which has an amplified receptor gene. EGF receptors from this cell line were immunoprecipitated with monoclonal antibody R1 as described in Example 2. To determine potential biologic activity of the peptides, immune complex kinase assays were performed after adding various concentrations of the peptides or EGF to the complexes and measuring autophosphorylation as described in Example 3 (See FIG. 1 and FIG. 2). Selected peptides from Example 3 were employed in the study.

Figure 1:
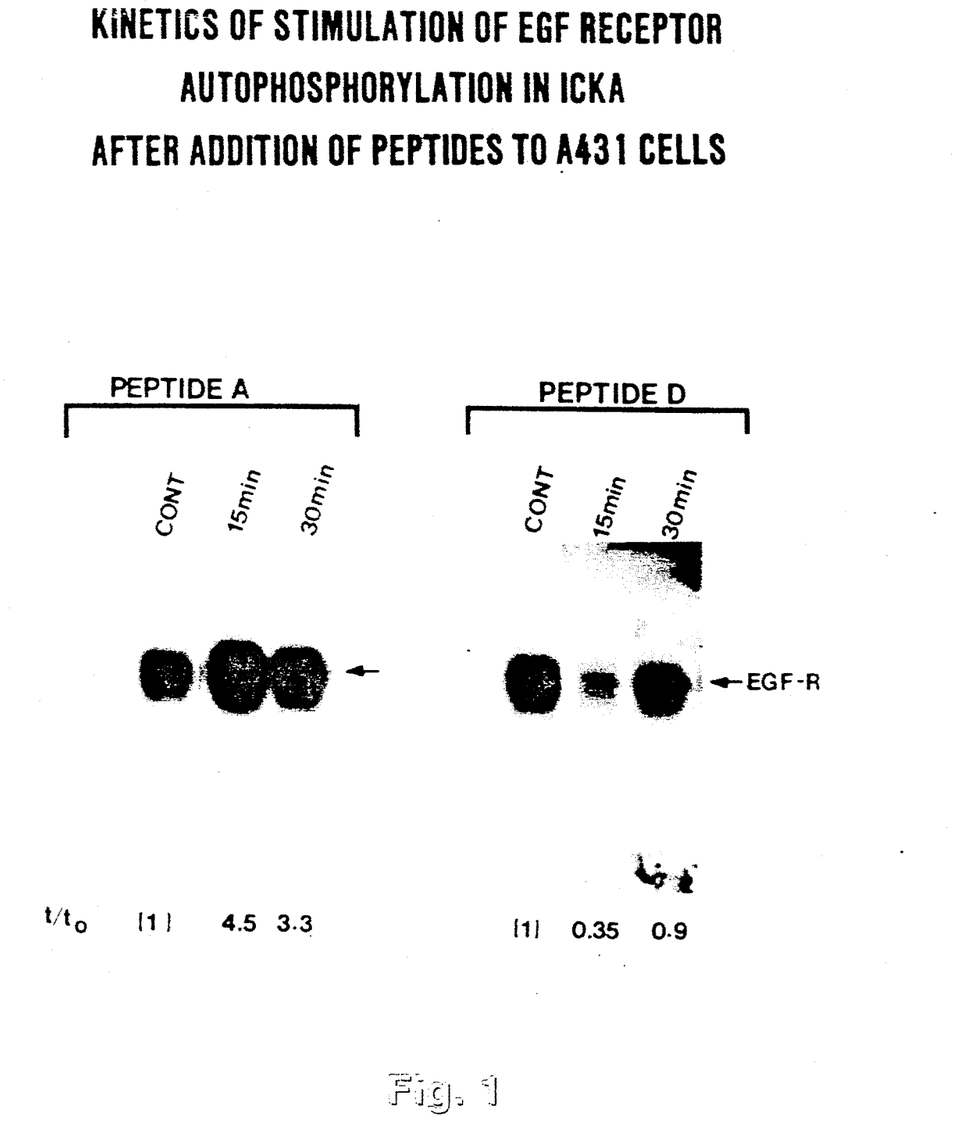

The results of the cyclic and linear peptide with tyrosine in position 6 (aa residue #37) compared to EGF are shown in FIG. 1. Peptide "A", (which corresponds to the cyclic form of the EGF peptide analog containing the natural tyrosine) exhibit great biologic activity in this assay, increasing the kinase activity 3 to 6-fold at a concentration of 20 ng/ml. This level of stimulation is approximately equivalent to native EGF at a concentration of 5 ng/ml. Small stimulation (approximately 2-fold) was observed at 30 ng/ml of the cyclic peptide analog which contained phenylalanine substituted at aa residue position 6 (aa residue 37), with the comparable linear peptide (phe-substituted) showing no activity (not shown).

Figure 2:
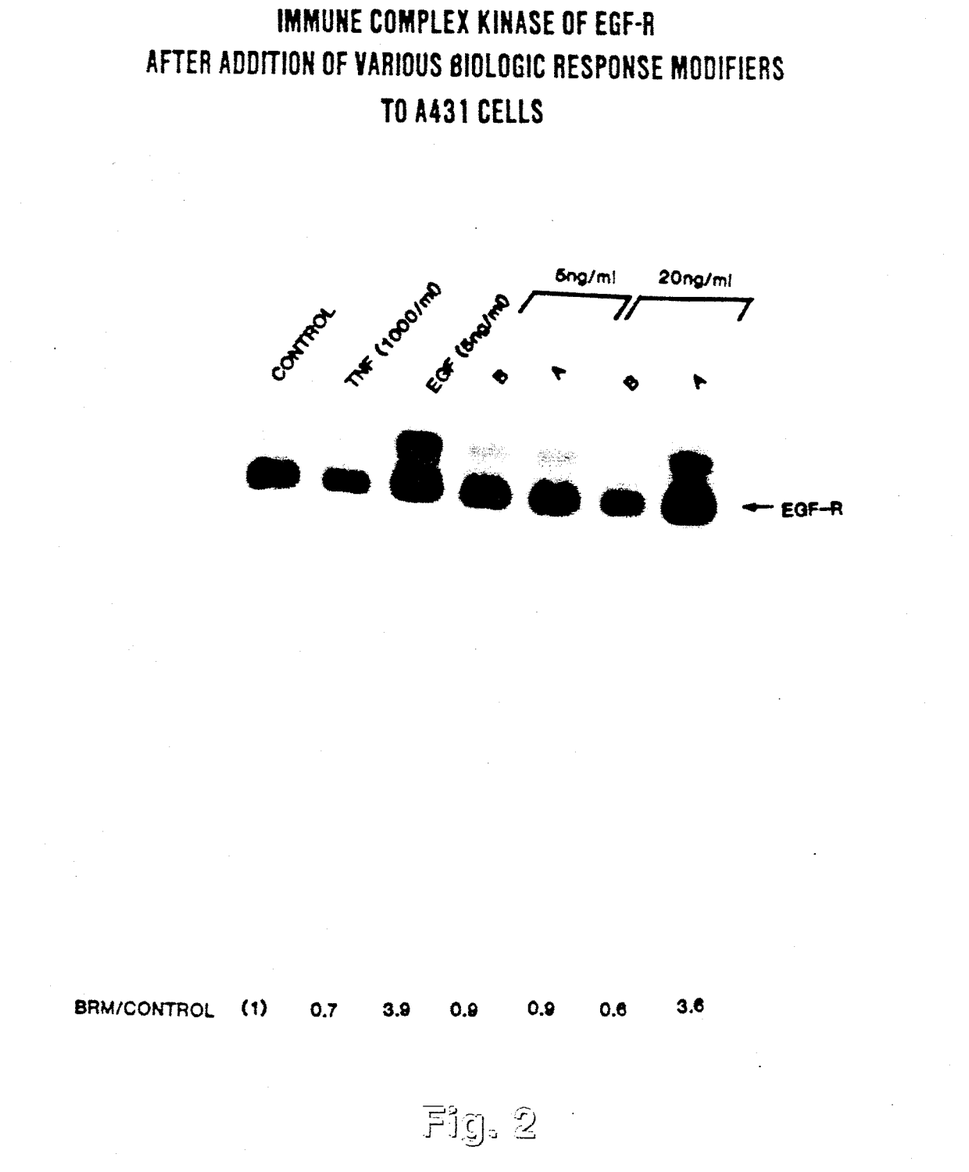

In very preliminary analyses of the kinetics of stimulation, the cyclic peptide (labeled peptide "A") showed maximum stimulation of kinase activity after 15 min (FIG. 2). Interestingly, peptide "D", which is the linear peptide with phenylalanine at aa residue position 37, inhibited kinase activity (FIG. 2).

EXAMPLE 5

EGF Receptor Competition Assays

The present experiment was designed to determine the binding site of the prepared peptide EGF analogs to EGF receptor.

Determination of whether or not peptides bind directly to EGF receptor may be difficult, because iodination of the peptides may interfere with the conformation. Therefore, for preliminary studies, Applicants chose to assess the ability of the EGF peptide analog to compete with native $^{125}$I-EGF for EGF-receptor binding sites. For this assay, cells were grown overnight in serum free media in microtiter wells, washed several times in PBS, then incubated for 2h with various concentrations of peptides. $^{125}$I-EGF was then added for 3o min, cells were extensively washed, and radioactivity was estimated in a gamma counter.

Figure 3:
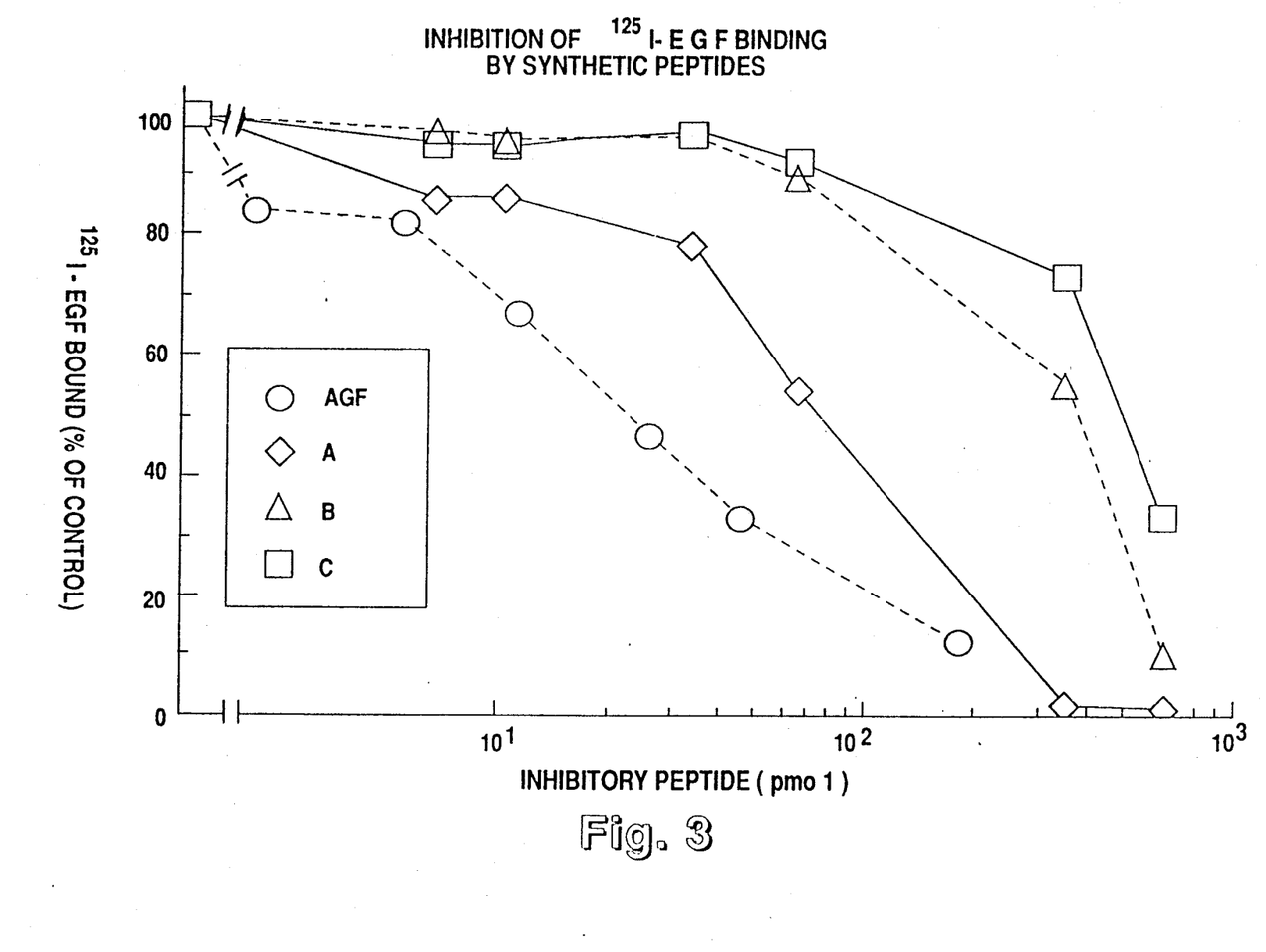

The results of this experiment are shown in FIG. 3. The cyclic peptide with tyr is labeled "A" in FIG. 3, and showed substantial competition with $^{125}$I-EGF for binding EGF receptor. 50% inhibition occurred at a concentration only 10-fold greater than that for unlabeled EGF. These results are significant, because they represent a 100-fold better competition by the synthetic EGF peptide analog for EGF receptor binding than any other peptide thus far reported.

The aa residue #37 substituted cyclic peptide (phenylalanine) (labeled "C" in FIG. 3) and the unsubstituted (tyrosine) linear peptide (labeled "B" in FIG. 3) show marginal competition for $^{125}$I-EGF binding. Unrelated cyclic peptides of similar length show very little ability to compete with EGF. Thus, the peptide most active in the kinase assay is also most active in inhibition of EGF binding. Differences in the biologic effectiveness of the peptides in these two assays thus do exist.

EXAMPLE 6

Inhibition of Ornithine Decarboxylase (ODC) Activity

Figure 4:
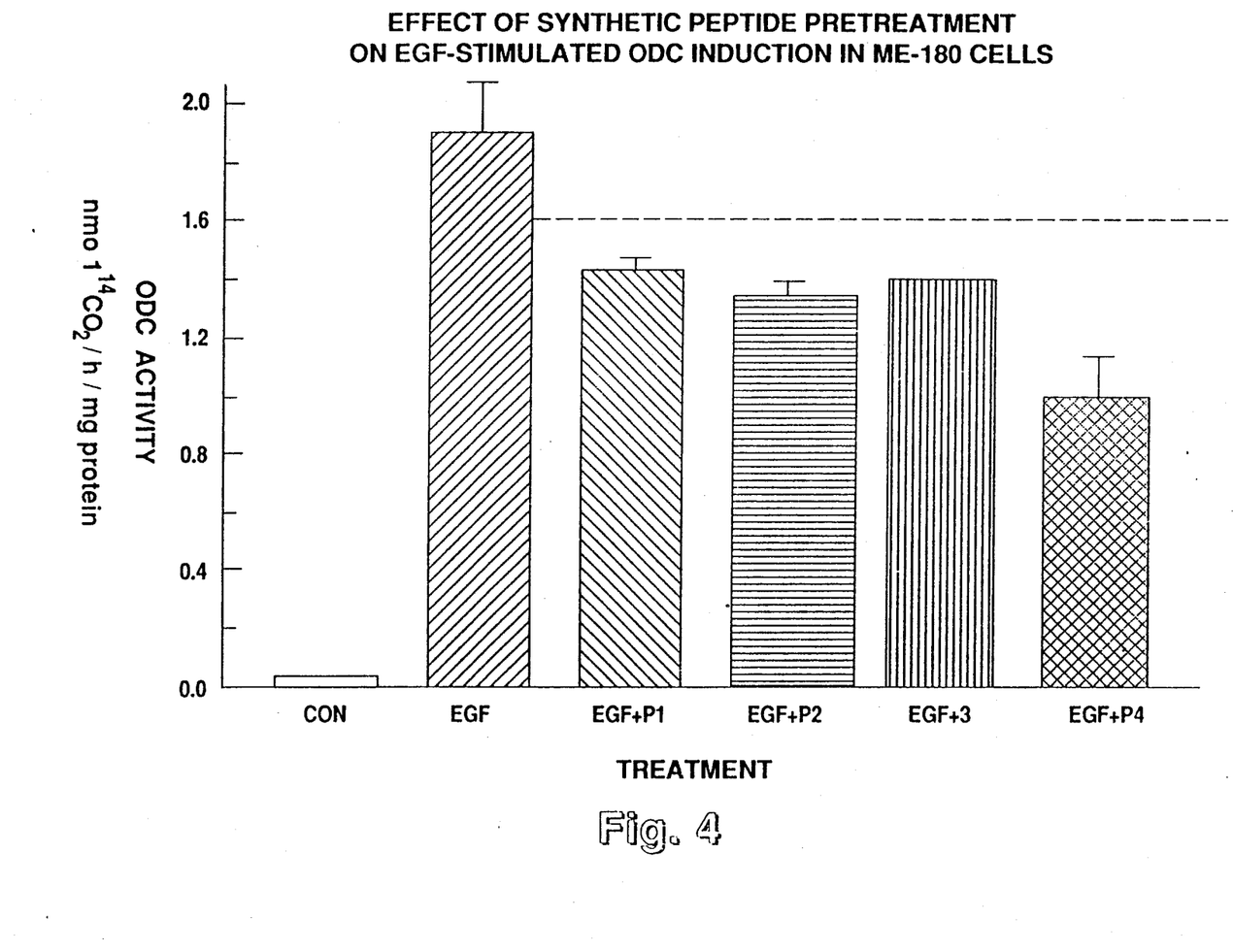

Ornithine decarboxylase is an enzyme whose activity is rapidly increased following mitogenic stimulation of cells by EGF (as well as many other growth factors). The results of Applicants' preliminary studies are shown in FIG. 4. The cyclic peptide with natural tyrosine at position 6, (aa residue #37 of the native peptide) labeled peptide 4 in FIG. 4, inhibited by 50% the ODC induction of EGF at 100-fold excess. Other peptides were less active. Thus, in all three assays, the same cyclic tyrosine monomer form of the EGF peptide analog between aa32 and aa48 of the native peptide was most active, strongly suggesting a specific interaction of the particular EGF segment which corresponds to this sequence in native EGF with EGF-r.

EXAMPLE 7

Mitogenic Stimulation of A431 Cells

Applicants initiated preliminary studies to determine if the peptide analog can simulate the effects of EGF on A431 cells (ATCC CRL 1555).

Figure 5:
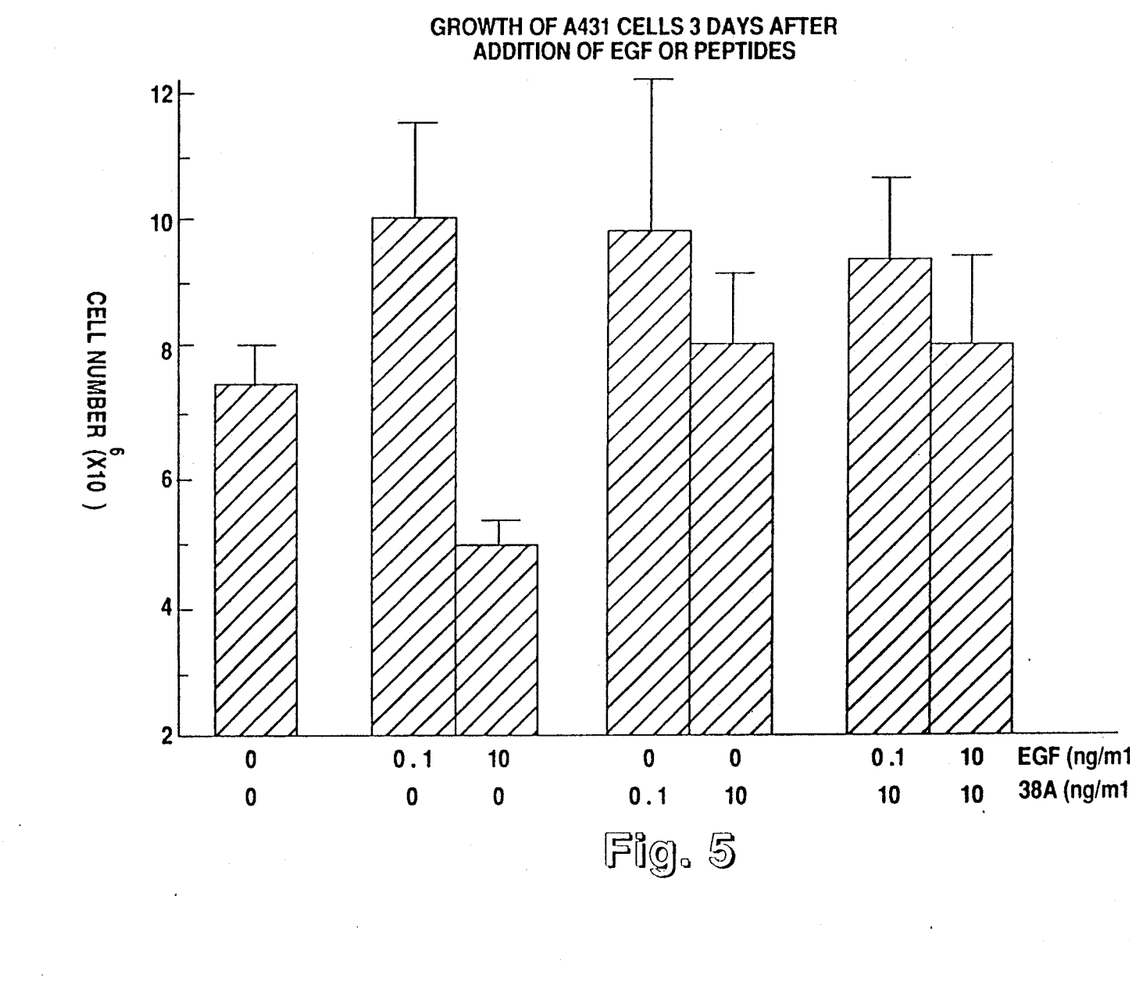
FIG. 5 —Effect of EGF or cyclic Peptide on the Growth of A431 cells. Mitogenic Stimulation of A431 cells. This study was performed to determine if the peptide analogs can simulate the effects of native EGF on A431 cells. Cells were seeded at a density of 2×10$^6$ in 60 mm diameter tissue culture plates, and grown in serum-free medium with the addition of peptide and/or EGF after 3 day incubation period. The peptide analog 38A is the cyclic form of the peptide with native tyrosine. Cells were harvested 72 hours later and counted with the aid of a hemacytometer. Native EGF stimulated growth of A431 cells at low concentrations (0.1 ng/ml) while the EGF inhibited cell growth at higher concentrations (10 ng/ml). The cyclic form of the Applicants' most biologically active cyclic of EGF peptide analog stimulated cell growth at both low (0.1 ng/ml) and high (10 ng/ml) concentrations. Over the range of concentrations tested, no inhibition of A431 cell growth was observed with the synthetic cyclic EGF peptide analog.

A431 cells are a malignant cell line in which the study of EGF-r has been well characterized. Cells were plated at a density of $2 \times 10^6$, and grown for three days with the addition of peptide analog and/or EGF, as shown in FIG. 5. As expected, at 0.1 ng/ml, EGF stimulated A431 cell growth. At 10 ng/ml EGF, growth of these cells was inhibited. Interestingly, at both 0.1 and 10 ng/ml, the most biologically active cyclic peptide analog also stimulated these cells. Over the range of peptide analog concentrations tested, no inhibition of A431 cell growth was observed.

In experiments in which peptide analog and EGF were mixed at the concentrations shown, stimulation of cell growth was observed at low concentrations. However, higher concentrations of EGF no longer growth-inhibited A431 cells in the presence of 10 ng/ml peptide analog.

These experiments strongly suggest that the cyclic peptide does possess biologic activity. In summary, the data demonstrates that the cyclic peptide under study interacts with EGF receptor, and may have important effects on the growth of cell lines.

EXAMPLE 8

Proposed Use of Synthetic EGF Peptide in Humans for Treatment of Tumors

Insofar as the presently disclosed cyclic peptide analogs of EGF have been demonstrated to have binding affinity for EGF receptor, Applicants propose the use of these peptides in the inhibition of tumorous or malignant cell growths comprised of cells which overexpress EGF receptor. Representative of this class of tumorous growths for example, are those squamous cell carcinomas, of the lung, head, and neck. Other tumorous growths of the brain, bladder and breast are also contemplated as within the scope of conditions effectively treatable with the described peptides.

While the optimum dose schedule needs to be determined following the standard phase I and II clinical trial format, one conceivable dose schedule would be like the one shown below. Initially, the first 3 patients will receive the peptide analog at a dose of 0.1 mg/m$^2$ given intravenously over one hour daily for 7 days under close monitoring of the vital signs and for any evidence of clinical toxicities, as an in-patient. This treatment will be followed by an additional observation period of 2 weeks. If all the 3 patients tolerate this treatment without any serious side effects (Grade III or IV, according to the modified WHO toxicity criteria[4]). Subsequent patients will be treated. These subsequent patients will be treated with escalating doses of the particular peptide analog, 3 patients per each dose level, according to the following scheme:

| Dose level | Dose (mg/m$^2$/day) | Treatment Duration |
| --- | --- | --- |
| 1 | 0.1 | 7 Days |
| 2 | 0.5 | 7 |
| 3 | 1.0 | 7 |
| 4 | 5.0 | 7 |
| 5 | 10.0 | 7 |
| 6 | 20.0 | 7 |
| 7 | 40.0 | 7 |
| 8 | 80.0 | 7 |
| 9 | 160.0 | 7 |
| | to maximum tolerance | |

As more experience is gained, other dose schedules such as continuous infusion of the peptide analog (i.e., 1-10 mg/m$^2$/hr for 3 weeks followed by 1 week off) or daily bolus injection (i.e., 10 mg/m$^2$/day for 3 weeks followed by one week off, or for even longer duration) are planned to be explored.

In terms of efficacy evaluation, Applicants plan to enroll a group of patients with clinically valuable and/or measurable tumor lesions such as enlarged lymph nodes and/or lesions in the lung or in the liver, which can be easily followed by physical examination and/or by radiographic evaluation including CAT scans. Response criteria[4] are quite standard and are well known to those of skill in the medical sciences. A complete remission is defined as complete disappearance of all clinical evidence of active tumor for a minimum of 4 weeks; a partial remission is defined as a 50% or greater decrease in the sum of the products of the diameters of the measured lesion lasting for a minimum of 4 weeks. There should be no simultaneous increase in the size of any lesion and no appearance of any new lesion.

Should this approach be hampered by stimulation of tumor growth, instead of growth inhibition, this property of the EGF peptide can be exploited to recruit the resting tumor cells into the cell cycle and then treat them with cycle-specific chemotherapeutic agents.

For these particular uses, the described peptides may well be conjugated to a chemotherapeutic agent via labile bonds. By way of example, these chemotherapeutic agents include cisplatinum, adriamycin, cytoxan, methotrexate, 5-fluorouracil, etoposide, or bleomycin. The described peptide may be coupled to a delivery system. By way of example, such a delivery system may include coupling of the peptide to a monoclonal antibody, diphtheria toxin, or other like agent. Coupling of the peptide to an appropriate carrier is contemplated to better facilitate the targeting of specific tumors.

More particularly, to approach the important prospect of using peptides as a specific ligand for drug delivery to tumor cells. Applicants propose to attach alkylating agents which have been used in chemotherapy to the amino terminus of active peptides via the acid labile cis aconitate bond as described by Dillman et al.[24]. On internalization of the receptor-ligand complexes, the cis-aconitate bond will be cleaved[24], freeing the drug and inducing cytotoxicity.

The biological characteristics of the described peptides thus makes them a potentially revolutionary anticancer therapeutic agent for human use. Also, preliminary cellular studies provide the basis upon which use of the described peptides to promote wound healing, especially ulcerogenic damage and burn wounds, is presented.

BIBLIOGRAPHY

The following references are specifically incorporated herein by reference:
1. Cooke, R. M., Wilkinson, A. J., Baron, M., Pastore, A., Tappin, J. J., Campbell, I. D., Gregory, J., and Sheard, B., (1987) *Nature*, 327:339–41.
2. Komoriya, A., Hortsch, M., Meyers, C., Smith, M., Kanety, H., and Schlessinger, J., (1984) *Proc. Natl. Acad. Sci. U.S.A.*, 81:1351–55.
3. Heath, W. F., and Merrifield, R. B., (1986), *Proc. Natl. Sci. U.S.A.*, 83:6357–71.
4. Gregory, J., (1975), *Nature*, 257:325–27.
5. Cohen, S.L. and Carpenter, G., (1985), *Proc. Natl. Acad. Sci. U.S.A.*, 72:1317–21.
6. Hollenberg, M. D. and Gregory, J., (1977), *Clin. Res.*, 25:312 (abstr).
7. Simpson, R. J., Smith, J. A., Moritz, R. L., O'Hare, M. J., Rudland, P.S., (1985), *Eur. J. Biochem.*, 153:629–37.
8. Engler, D. A., Matsunami, R. K., Campion, S. R., String, C. D., Stevens, A. and Niyogi, S. K., (1988), *J. Biol. Chem.* 263(25):12384–90.
9. Merrifield, (1963), *J. Am. Chem. Soc.*, 85:2144–54.
10. Chang, et al., (1980), *Int. J. Peptide Protein Res.*, 15:485–94.
11. DeLarco, J. E., et al., (1978), *Proc. Natl. Acad. Sci.*, 75: 4001–04.
12. Nestor, et al., (1985), *Biochem. Biophys. Res. Comm.*, 129(1);226–32.
13. Rivier, et al., (1974), *J.A.C.S.*, 96:2986–92.
14. Libermann, T. A., et al., (1985), *Nature*, 313: 144–47.
15. Gusterson, B., et al., (1984), *Cell Biol. Int. Rep.*, 8: 649–57.
16. Fitzpatrick, S. L., et al., (1984), *Cancer Res.*, 44:3448–53.
17. Derynck, R., et al., (1987), *Cancer Res.*, 47: 702–12.
18. Cohen, S. (1962), *J. Biol Chem*, 237: 1555–62.
19. Carpenter (1987), *Annu Rev Biochem* 56:881–914.
20. Carpenter (1979), *Annu Rev Biochem*, 48: 193–216.
21. Kamata, N., et al. (1986), *Cancer Res*, 46: 1648–53.
22. Schlessinger, et al. (1983), *CCR Crit. Rev. Biochem.*, 14:43–111.
23. Cohen, et al. (1978), *Rec. Prog. Horm. Res.*, 30:551–72.
24. Dillman, et al. (1988), *Cancer Res.*, 48:6097–6102.
25. Miller, et al. (1981), *Cancer*, 47:207–14.
26. Maxwell (1989), *Cancer Res.*, 49(5):1130–7.

What is claimed is:

1. A biologically active peptide fragment of EGF peptide consisting essentially of NCVVGYIGERCQYRDLK having a carboxyl end amide group and an amino end acetyl.

2. A biologically active peptide fragment of epidermal growth factor consisting essentially of NCVVGYIGERCOYRDLK, wherein said peptide is capable of inhibiting tumor cell growth, promoting wound healing, and binding EGF receptors, and wherein said peptide is further defined as consisting of a carboxyl end amide group and an amino end acetyl group.

3. A biologically active cyclic peptide fragment of EGF consisting essentially of NCVVGYIGERCQYRDLK, having a carboxyl end amide group and an amino end acetyl group and wherein the cysteines of said sequence form an internal disulfide bond.

4. The peptide analog of epidermal growth factor defined in claim 1 or 2, further defined as comprising a cyclic peptide.

5. The biologically active peptide fragment of claim 1, 2, or 3, defined as having greater than 0.001% of the binding affinity of native EGF for EGF receptors.

6. The peptide of claim 1, 2, 3 or 4, further defined as protease resistant.

7. The peptide of claim 1, 2, 3 or 4, further defined as comprising a B loop end fragment and a C loop characteristic of native epidermal growth factor.

8. The peptide of claim 1, 2, 3 or 4, further defined as capable of inhibiting ornithine decarboxylase activity in a cell line.

9. The peptide of claim 8, wherein the cell line is A418.

10. The peptide analog of claim 1, 2, 3 or 4, further defined as comprising L-amino acids or D-amino acids.

11. The peptide analog of claim 1, 2, 3 or 4, further defined as comprising D-amino acids.

12. The peptide analog of claim 1 or 2, further comprising an internal bond between the two cysteines within the peptide.

13. The biologically active cyclic peptide fragment of claim 3 defined as having at least 4.5% the binding affinity of native EGF for EGF receptors.

14. The biologically active cyclic peptide of claim 3 defined as having about 18% the binding affinity of native EGF for EGF receptors.

15. A biologically active cyclic peptide fragment of EGF defined as consisting essentially of an amino acid sequence NCVVGFIGERCQYRDLK, wheel the cysteines of said peptide form a disulfide bond, and wherein said peptide consists of a carboxyl end amide group and an amino end acetyl group.

16. The biologically active peptide fragment of claim 15 defined as having binding affinity for A-413 cell EGF receptors, inhibiting tumor cell growth, and promoting wound healing.

* * * * *

UNITED STATES PATENT AND TRADEMARK OFFICE
CERTIFICATE OF CORRECTION

PATENT NO.: 5,183,805
DATED: February 2, 1993
INVENTOR(S): Gallick et al.

It is certified that error appears in the above-identified patent and that said Letters Patent is hereby corrected as shown below:

In claim 2, line 38, column 16 delete "O" and insert --Q--, therefor.

In claim 5, line 53, column 16, the word "of" was inadvertently inserted during printing, but can remain there.

In claim 15, line 3, column 18, delete the term "wheel" and insert --wherein--, therefor.

On the cover page, first column, [75] after "Blick," add --Gary E. Gallick and Ralph Arlinghaus--, therefor; delete "both" and insert --all--, therefor.

Signed and Sealed this

Ninth Day of November, 1993

Attest:

BRUCE LEHMAN

Attesting Officer

Commissioner of Patents and Trademarks